United States Patent [19]

Gold

[11] 4,230,101

[45] Oct. 28, 1980

[54] BACK BRACE

[76] Inventor: Jack Gold, 4 Hillary Ct., Livingston, N.J. 07039

[21] Appl. No.: 937,611

[22] Filed: Aug. 28, 1978

[51] Int. Cl.³ .............................................. A61F 5/02
[52] U.S. Cl. ................................................... 128/78
[58] Field of Search ...................... 128/78, 87 C, 89 R

[56] References Cited

U.S. PATENT DOCUMENTS

| | | | |
|---|---|---|---|
| 1,931,990 | 10/1933 | Mussack | 128/78 |
| 3,945,376 | 3/1976 | Kuehnegger | 128/78 |

FOREIGN PATENT DOCUMENTS 2449761  4/1975  Fed. Rep. of Germany ........ 128/87 R

OTHER PUBLICATIONS

"An Easier Way to Make a Milwaukee Brace", Bonnett, M. D., et al., Orthopaedic Review, vol. V, No. 2, Feb. 1976, pp. 47-52.
Webster's Seventh New Collegiate Dictionary, 1963, G. C. Merriam Co., Springfield, Mass., 1963, p. 353.
Orthopaedic Appliances Atlas, vol. 1, J. W. Edwards-Ann Arbor, Michigan-1952, pp. 218-219.
Lancet "Plastic Appliances Moulded Direct to Patient", vol. 268, p. 841, Apr. 23, 1955.

*Primary Examiner*—Robert W. Michell
*Assistant Examiner*—J. L. Kruter
*Attorney, Agent, or Firm*—H. Hume Mathews

[57]  ABSTRACT

A back brace for the treatment of scoliosis having posterior and auterior metal uprights secured to a pelvic girdle and extending vertically upward to a level just below the level of the patient's clavicles, and having laterally extending arms fastened to the upper portions of said vertical uprights for encircling the space to be occupied by the upper torso of the patient at the level of, and just below, the patient's armpits.

1 Claim, 6 Drawing Figures

FIG. 4
FIG. 5
FIG. 6
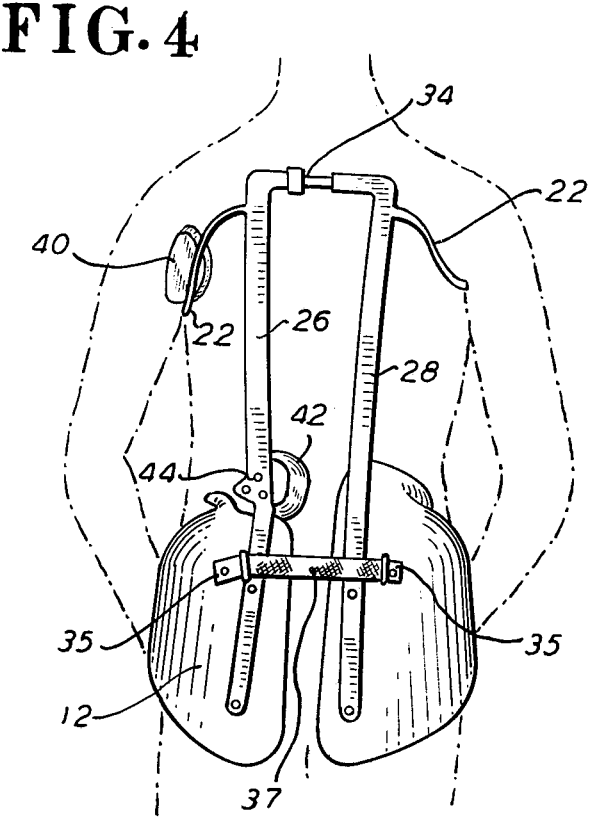
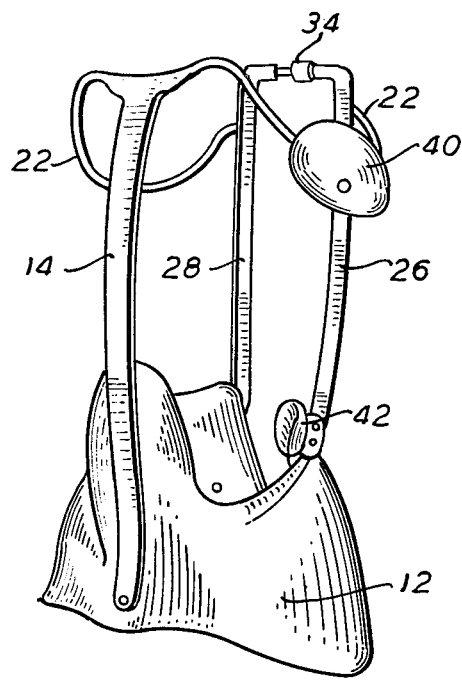
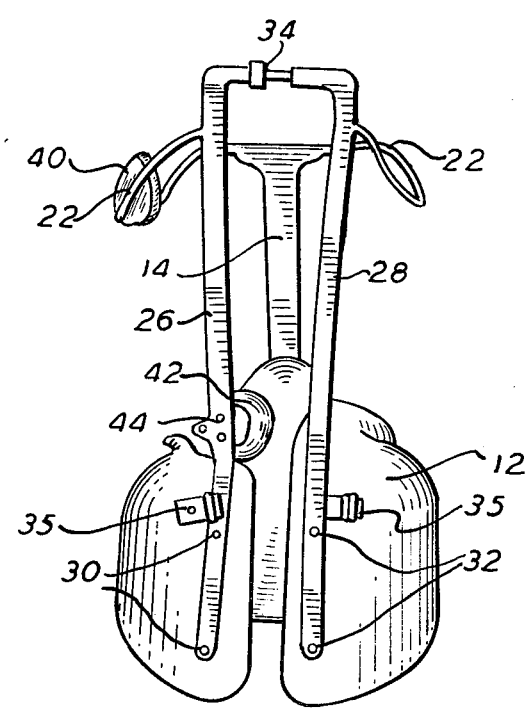

BACK BRACE

BACKGROUND OF THE INVENTION

Back braces for the correction of curvature of the spine (scoliosis) have been known for more than a hundred years.

Beginning about 1946, the Milwaukee Brace was developed, to provide an apparatus whereby some types of scoliosis can be treated without surgery.

The Milwaukee Brace consists of a neck ring, having attached pads for directing pressure against the occiput and the chin, and a pelvic girdle. These two sections originally were joined by two upright metal bars in front and two behind. Turnbuckles in the center of these metal uprights permitted increasing amounts of distraction to be applied.

In the late 50's and early 60's the Milwaukee Brace came into increasing use in an ambulatory method of correcting spinal curves in growing children.

Improvements in the Milwaukee Brace have been made over the years. The present Milwaukee Brace (prior to the present invention) consists of a pelvic girdle, two uprights in the back and one upright in the front, all of which are adjustable. A throat pad is connected to the ciphalad portion of the uprights. To this are attached the throat mold and the occiput.

The present invention relates to still further improvement in the Milwaukee type of brace, wherein the neck ring, and the upper segments of the anterior and posterior bars, are eliminated.

Corset types of braces having no neck ring have previously been known, but such corset type braces are made completely of plastic and are not really of the Milwaukee type because they lack metal uprights. They are of only limited usefulness, being applicable only for the treatment of "low curve" backs as distinguished from the "high curve" backs to which the Milwaukee Brace, and the improved brace of the present invention, may be applied for treatment.

SUMMARY OF THE INVENTION

According to the present invention, a brace of the Milwaukee type, having a pelvic girdle to which two metal uprights are attached in back and one metal upright is attached in front, is provided with an upper bust or chest ring that extend around the patient's trunk, underneath the armpits, just below the level of the clavicles. This chest ring is attached to the top of the front metal upright and to the tops of the two back metal uprights. The neck ring used in the Milwaukee Brace of the prior art is eliminated completely in the improved brace of the present invention. The upper segments of both anterior and posterior bars are also eliminated.

The improved brace of the present invention can be used for the treatment of scoliosis, including particularly the treatment of "high curve" backs, as effectively as the Milwaukee Brace of the prior art. However, the novel brace of the present invention will in addition offer the patient much more comfort, so that it can be worn comfortably almost twenty-four hours of each day. Further, it can be worn completely under the patient's clothes, with resultant improvement in the patient's appearance. As a result, some patients who disliked to wear, or even refused to wear the prior art Milwaukee Brace, will wear the improved brace of the present invention.

BRIEF DESCRIPTION OF THE DRAWING

FIG. 4 is a rear elevation of the back of a patient wearing the improved brace of the present invention.

FIG. 5 is a front elevation of the brace alone, facing slightly to the left of the central position.

FIG. 6 is a rear elevation of the brace alone.

DETAILED DESCRIPTION OF A PREFERRED EMBODIMENT OF THE INVENTION

Figure 1:
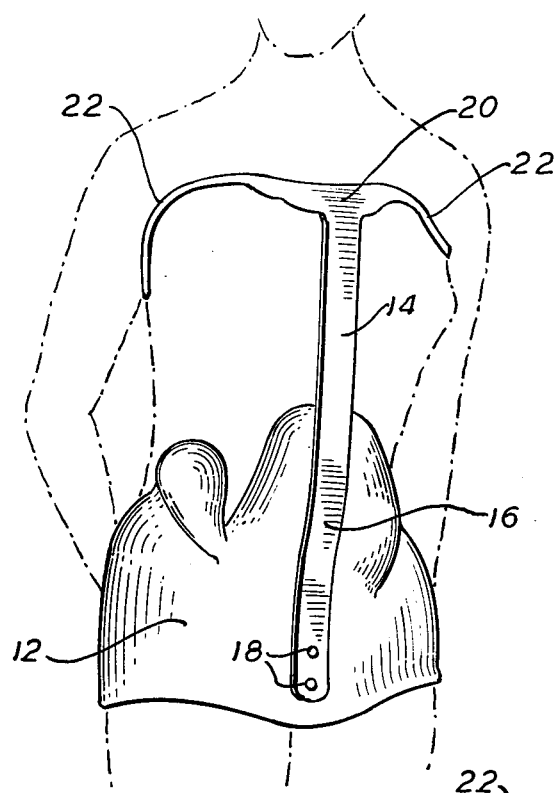
FIG. 1 is a front elevation of a patient wearing the improved brace of the present invention, with the patient facing slightly to the right of the central position.
Figure 2:
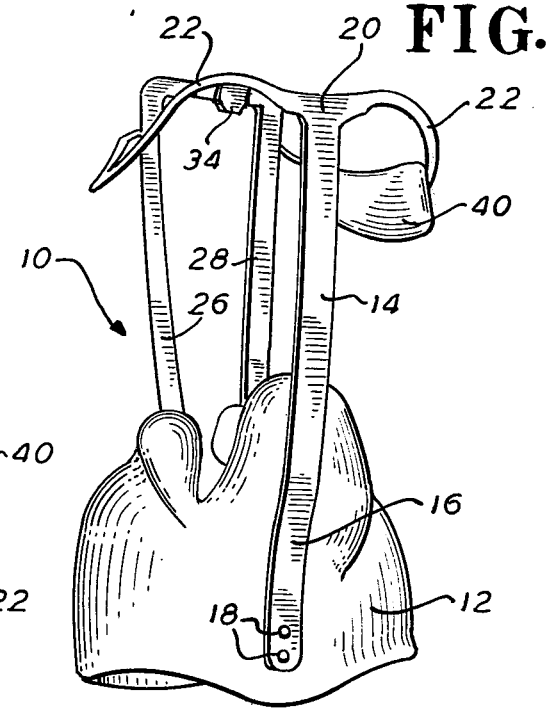
FIG. 2 is a view like FIG. 1 but of the brace alone; prior to application to the patient.
Figure 3:
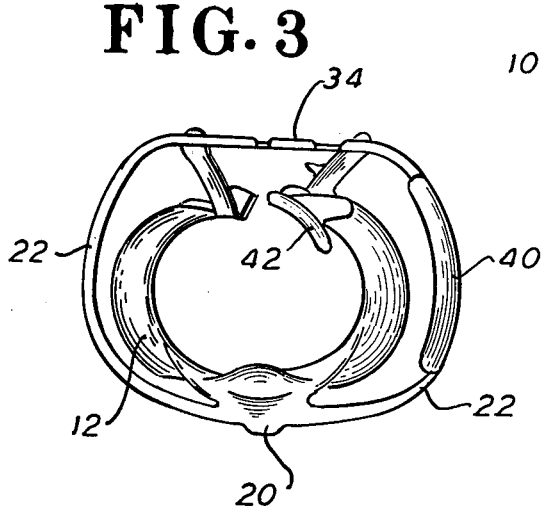
FIG. 3 is a top view of the brace of FIG. 2.

The brace 10 as shown in the drawings comprises a pelvic girdle 12 made preferably of a rigid plastic material which is molded to fit closely about the lower stomach and pelvic portion of the patient to whom the brace is to be applied. A rigid front metal upright 14, of strap or bar stock, extends upwardly from the girdle to a point substantially below the neck of the patient, terminating just below the level of the clavicles. This front brace is contoured, as shown at 16 to the curvature of the front of the patient. It is fixed to the girdle 12 by rivets 18 and terminates in a T connection 20 with laterally extending arms 22 at the top of the brace.

Arms 22 extend respectively around the upper portion of the patient's torso, just under the patient's arms, and join at the back with two laterally spaced rigid metal uprights 26, 28 rigidly connected to the back of girdle 12 by rivets 30, 32. Uprights 26, 28 are in turn joined at their tops by a separable joint as shown at 34. The pelvic girdle 12 also is formed with a posterior separable joint which may be secured after the brace is applied to the patient by buckles and a strap 37. All the said uprights are formed of rigid straps or bars, of metal such as stainless steel, and all the said joints and connections can be made tight or rigid. Thus the uprights and laterally extending arms 22 from what could be called a metal "cage", supported in substantially fixed position relative to the girdle 12 and relative to the hips and pelvic structure of the patient on which the girdle is secured.

The arrangement is such that the encircling arms 22 are maintained by uprights 14, 26 and 28 in a predetermined position relative to girdle 12, and are substantially fixed against displacement relative to the said girdle, particularly lateral displacement. Accordingly, once the brace of this invention is applied to a patient, the upper portion of the patient's torso, at the level of the encircling arms 22, will be maintained in a fixed lateral position, determined by the fitting or adjustment of the brace, relative to the pelvic portion of the patient's body.

In order that pressure may be applied to the patient's body at proper locations, for treatment and/or correction of the patient's scoliosis, pads are fixed to the brace structure at selected points, as respectively shown in the drawings at 40 and 42.

Adjustment devices, such as the adjustment screw 44 on pad 42 are provided so that pressure can be exerted on the patient's body at a particular place, and thus force the patient's body to a position in which the spinal curve is either reduced or eliminated.

Experimental application to patients of the improved brace of the present invention, in alternation with the prior art Milwaukee Brace having the conventional neck ring, has shown that the brace of this invention can be utilized to accomplish the same or similar results in treatment of scoliosis as the Milwaukee Brace, but without the discomfort and adverse effect on the patient's appearance which is inherent in use of the prior art Milwaukee Brace.

1 claim:

1. In a back brace for the treatment of scoliosis in a patient, said brace comprising, a rigid, molded plastic pelvic girdle shaped to fit closely about the lower stomach and pelvic portion of a patient, said girdle adapted to substantially surround the patient and coming together in a separable posterior joint, a pair of posterior rigid metal uprights, one of said uprights positioned on each side of said posterior joint, a single anterior rigid metal upright fastened substantially centrally of said girdle and extending vertically upward and adapted to fit the curvature of the front of the patient, each of said uprights terminating at a level just below the level of a patient's clavicle, laterally extending rigid metal arms fastened to the upper portions of said uprights and curved so as to be adapted to encircle the body of the patient at the approximate level of the patient's armpits, underneath the patient's arms, means on said girdle to secure the joint portions of the girdle together and means on the upper portions of said pair of posterior uprights to secure them to each other thereby forming a closed brace adapted to surround the patient, and means associated with a selected portion of at least one of the upright members and at least one of the encircling members for applying pressure to selected portions of the patient's body so that an abnormal curve of the patient's spinal column may be either reduced or eliminated by lateral pressure applied to the patient's body through said metal uprights.

* * * * *